United States Patent [19] [11] 4,067,981
Sasse et al. [45] Jan. 10, 1978

[54] 7-SUBSTITUTED-BENZO-1,2,4-TRIAZINE-3-ETHERS

[75] Inventors: Klaus Sasse, Schildgen; Paul-Ernst Frohberger; Hans Scheinpflug, both of Leverkusen, all of Germany

[73] Assignee: Bayer Aktiengesellschaft, Leverkusen, Germany

[21] Appl. No.: 717,969

[22] Filed: Aug. 26, 1976

[30] Foreign Application Priority Data

Aug. 27, 1975 Germany .............................. 2538179

[51] Int. Cl.$^2$ ...................... C07D 253/08; A01N 9/22
[52] U.S. Cl. ...................................... 424/249; 544/183
[58] Field of Search .................. 260/248 AS; 424/249

[56] References Cited

U.S. PATENT DOCUMENTS

| 2,489,354 | 11/1949 | Wolf et al. ............................ 260/248 |
| 3,349,088 | 10/1967 | Molnar et al. ................. 260/248 AS |
| 3,562,270 | 2/1971 | Wagner-Jauregg et al. .... 260/248 X |

FOREIGN PATENT DOCUMENTS 83,869 8/1971 Germany.

OTHER PUBLICATIONS

Chemical Abstracts, vol. 44, 10718(h), (1950).
Chem. Ber, vol. 102, pp. 3818–3823, (1969).

Primary Examiner—John M. Ford
Attorney, Agent, or Firm—Burgess, Dinklage & Sprung

[57] ABSTRACT

7-Substituted-benzo-1,2,4-triazine-3-ethers of the formula

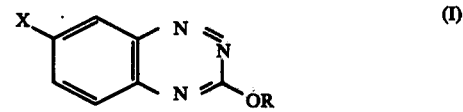

in which
R is alkyl with up to 8 carbon atoms optionally substituted by halogen or lower alkoxy, or alkenyl with 3 to 6 carbon atoms, and
X is halogen, trifluoromethyl or alkoxy with up to 4 carbon atoms,
which possess fungicidal, bactericidal, insecticidal and acaricidal properties.

10 Claims, No Drawings

7-SUBSTITUTED-BENZO-1,2,4-TRIAZINE-3-ETHERS

The present invention relates to and has for its objects the provision of particular new 7-substituted-benzo-1,2,4-triazine-3-ethers which possess fungicidal, bactericidal, insecticidal and acaricidal properties, active compositions in the form of mixtures of such compounds with solid and liquid dispersible carrier vehicles, and methods for producing such compounds and for using such compounds in a new way especially for combating pests, e.g. fungi, bacteria, insects and acarids, with other and further objects becoming apparent from a study of the within specification and accompanying examples.

Several 3-alkoxy-benzo-1,2,4-triazines have already been disclosed but these contain no further substituents on the benzene nucleus of the phenylene radical. Thus, 3-methoxy-benzo-1,2,4-triazine (Compound A) has been prepared by the action of diazomethane on 3-hydroxy-benzo-1,2,4-triazine (Rec. Faculte Sci. Univ. Istanbul 15 A, No. 2, 91-107 (1950) and Chem. Abstr. 44, 10,718 (1950)). 3-Ethoxy-benzo-1,2,4-triazine (Compound B) has been obtained by reacting 3-chloro-benzo-1,2,4-triazine with ethanol in the presence of sodium cyanide (Chem. Ber. 102, 3818 (1969)). Biological actions of these compounds have not been disclosed hitherto. Furthermore it is known from German DL Patent No. 83,869) that 3-alkoxy-benzo-1,2,4-triazine 1-oxides exhibit herbicidal and acaricidal properties. Fungicidal properties are not indicated for these compounds. An action against *Aspergillus niger, Botrytis cinerea, Rhizoctonia solani* and *Fusarium columorum* has been demonstrated in vitro only for the more remotely related 3-chloro-benzo-1,2,4-triazine 1-oxides.

The present invention provides 7-substituted-benzo-1,2,4-triazine-3-ethers of the general formula

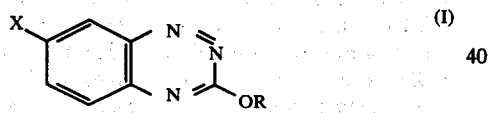

in which
R is alkyl with up to 8 carbon atoms optionally substituted by halogen or lower alkoxy, or alkenyl with 3 to 6 carbon atoms, and
X is halogen, trifluoromethyl or alkoxy with up to 4 carbon atoms.

Preferably, R represents straight-chain or branched alkyl with up to 6 carbon atoms which may optionally be monosubstituted or polysubstituted by chloride, bromine or alkoxy with up to 4 carbon atoms, or represents alkenyl with 3 to 6 carbon atoms, and X represents chlorine, bromine, trifluoromethyl or alkoxy with up to 3 carbon atoms.

Surprisingly, the benzo-1,2,4-triazine-3-ethers according to the invention display a powerful fungicidal action against phytopathogenic pathogens, especially those which attack cereal plants. The action against *Helminthosporium* species is particularly valuable since no adequately effective non-toxic preparations for this purpose have been available hitherto in practice, and thus it has hitherto been possible only with difficulty completely to replace cereal dressings based on the highly toxic organo-mercury compounds. Moreover, the compounds of the formula (I) possess a considerable bactericidal action. The substances according to the invention are thus valuable plant protection agents and represent an enrichment of the art.

The invention also provides a process for the production of benzo-1,2,4-triazine-3-ethers of the formula (I) in which
a. a 3-halo-benzo-1,2,4-triazine of the formula

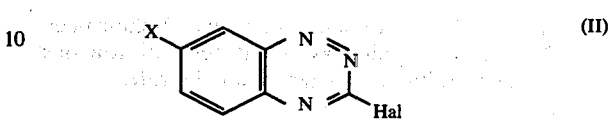

in which
X has the aforementioned meaning and
Hal represents chlorine or bromine,
is reacted with an alcohol of the formula

in which
R has the abovementioned meaning, in the presence of an acid-binding agent in the form of a metal alcoholate corresponding to the alcohol of the formula (III) or
b. a benzo-1,2,4-triazine-3-ether 1-oxide of the formula

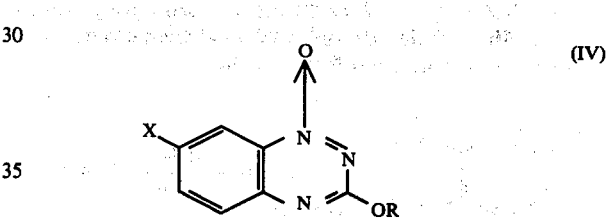

in which
R and X have the abovementioned meanings, is reacted with a reducing agent performing the required reduction, or
c. a 1,2-dihydrobenzo-1,2,4-triazine-3-ether of the formula

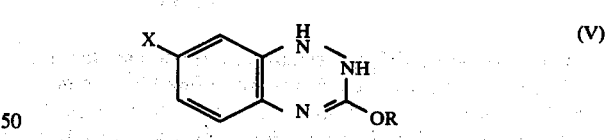

in which
R and X have the abovementioned meanings, is reacted with an oxidizing agent performing the required oxidation.

The process variants (a), (b) and (c) proceed as exemplified in the following reaction schemes.

In variant (a), for example, 3,7-dichlorobenzo-1,2,4-triazine may be reacted with isopropanol in the presence of sodium cyanide:

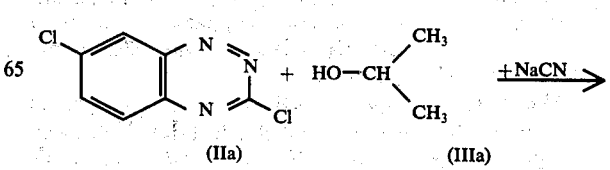

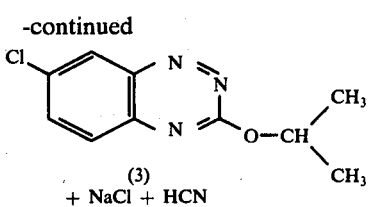
+ NaCl + HCN

In variant (b), for example 3-methoxy-7-chloro-benzo-1,2,4-triazine 1-oxide may be reduced with zinc dust in an aqueous solution of ammonium chloride:

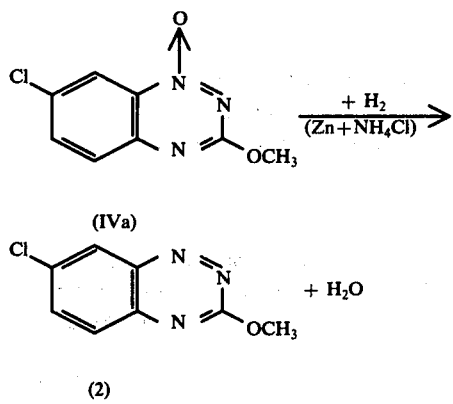

In variant (c), for example, 3-isopropoxy-7-trifluoromethyl-1,2-dihydro-benzo-1,2,4-triazine may be oxidized with potassium ferricyanide:

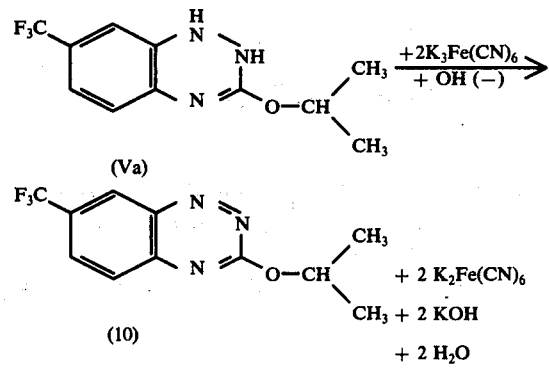

The 3-halo-benzo-1,2,4-triazines to be used as starting materials for process variant (a) are defined by the general formula (II). According to J. Org. Chem. Vol. 24 (1949) page 813, 3-chloro-benzo-1,2,4-triazine, unsubstituted on the benzene nucleus, i.e. X = H, is obtained by reducing 3-chlorobenzo-1,2,4-triazine 1-oxide with zinc dust in an aqueous solution of ammonium chloride. 3-Chloro-benzo-1,2,4-triazines (II) substituted on the benzene nucleus for use in the process according to the invention can be prepared from correspondingly substituted 3-chloro-benzo-1,2,4-triazine 1-oxides in a completely analogous manner. Examples of the starting materials of the formula (II) which may be mentioned are: 3,7-dichloro-benzo-1,2,4-triazine, 3-chloro-7-bromo-benzo-1,2,4-triazine, 3-chloro-7-iodo-benzo-1,2,4-triazine, 3-chloro-7-methoxy-benzo-1,2,4-triazine, 3-chloro-7-isopropoxy-benzo-1,2,4-triazine, 3-chloro-7-trifluoromethylbenzo-1,2,4-triazine and 3-bromo-7-chloro-benzo-1,2,4-triazine.

The alcohols which are also required for process variant (a) are defined by the formula (III). These alcohols are generally known substances customary in the laboratory. Individual examples which may be mentioned are: methanol, ethanol, propanol, isopropanol, butan-1-ol, iso-butanol, sec.-butanol (butan-2ol), pentanol (amyl alcohol), 2-methyl-butan-4-ol (isoamyl alcohol), 2,2-dimethyl-propanol (neopentyl alcohol), hexan-1-ol, 2-methyl-pentan-4-ol, 2-ethyl-butan-1-ol, 2-chloro-ethanol, 2,2,2-trichloro-ethanol, 2,3-dibromo-propan-1-ol, 1-chloro-propan-2-ol, 1,3-dichloro-propan-2-ol, allyl alcohol, 2-methyl-but-3-en-2-ol, 2-methoxy-ethanol, 2-butoxy-ethanol and 3-methoxy-propanol.

The 3-alkoxy-benzo-1,2,4-triazine 1-oxides which are required as starting materials for process variant (b) are defined by the general formula (IV). As a rule, they are obtained by the action of alcohols on 3-chloro-benzo-1,2,4-triazine 1-oxides in the presence of acid-binding agents. Thus, the 3-ethoxy- and 3-butoxy-benzo-1,2,4-triazine 1-oxides which are unsubstituted in the benzene nucleus have been prepared by reacting 3-chloro-benzo-1,2,4-triazine 1-oxide with ethanol and butanol respectively, in the presence of sodium cyanide, potassium carbonate or potassium fluoride as the acid acceptor (compare J. Org. Chem. 24, 813 (1959)). An alternative process is to react the 3-chloro-benzo-1,2,4-triazine 1-oxides with metal alcoholates, such as has been described for the homologous series of the 3-alkoxy-benzo-1,2,4-triazine 1-oxides which are unsubstituted in the benzene nucleus (compare German DL Patent No. 83,869). 3-Alkoxy-benzo-1,2,4-triazine 1-oxides (IV) which have halogen, alkoxy or trifluoromethyl substituents in the phenylene radical and which are required according to the invention can be prepared completely analogously and are described in French Patent No. 1,440,629. 3-chloro-benzo-1,2,4-triazine oxides which are required as precursors for the preparation of the starting materials of the formula (IV) have also previously been described in the literature. As a rule they are obtained from the corresponding 3-hydroxy-benzo-1,2,4-triazine 1-oxides by reaction with phosphorus oxychloride (see, for example, J. Org. Chem. 24, 813 (1959) and German DL Patent No. 83,869). Examples which may be mentioned of the starting materials of the formula (IV), the radicals R and X of which also correspond to the starting materials of the formula (V), are: 3-methoxy-7-chloro-benzo-1,2,4-triazine 1-oxide, 3-ethoxy-7-chloro-benzo-1,2,4-triazine 1-oxide, 3-isopropoxy-7-chloro-benzo-1,2,4-triazine 1-oxide, 3-propoxy-7-chloro-benzo-1,2,4-triazine 1-oxide, 3-butoxy-7-chloro-benzo-1,2,4-triazine 1-oxide, 3-hexyloxy-7-chloro-benzo-1,2,4-trazine 1-oxide, 3-allyloxy-7-chloro-benzo-1,2,4-triazine 1-oxide, 3-(2-chloroethoxy)-7-chloro-benzo-1,2,4-triazine 1-oxide, 3(2,2,2-trichloro-ethoxy)-7-chloro-benzo-1,2,4-triazine 1-oxide, 3-isopropoxy-7-bromo-benzo-1,2,4-triazine 1-oxide, 3-isopropoxy-7-methoxy-benzo-1,2,4-triazine 1-oxide, 3-methoxy-7-isopropoxy-benzo-1,2,4-triazine 1-oxide and 3-methoxy-7-trifluoromethyll-benzo-1,2,4-triazine 1-oxide.

7-Substituted-1,2-dihydrobenzo-1,2,4-triazine-3-ethers which are required as starting materials for process variant (c), defined by the general formula (V), of the formula (V) are also described in French Patent No 1,440,629. The compounds of the formula (V) which have specific substituents R and X according to the invention can be prepared analogously, according to methods known from the literature. Preferably, these compounds are obtained by reducing 7-substituted-benzo-1,2,4-triazine-3-ether 1-oxides with metallic tin in the presence of mineral acids, for example with hydrochloric acid, such as has also been described elsewhere (J. Org. Chem. 24, 813 (1959)) for 3-amino-1,2-dihydrobenzo-1,2,4-triazines.

In process variant (a), 3-halo-benzo-1,2,4-triazines of the formula (II) are reacted with alcohols of the formula (III). These reactions may be carried out in a diluent. Diluents which can be used include all organic solvents which are inert towards the compounds (II), for example aliphatic and aromatic hydrocarbons and chlorinated hydrocarbons, such as ligroin, benzene, toluene, chlorbenzene, methylene chloride, carbon tetrachloride; ethers, such as diethyl ether, diisopropyl ether, dioxane and tetrahydrofuran; ketones, such as acetone, methyl ethyl ketone and cyclohexanone; and dimethylformamide and dimethylsulfoxide. However, the alcohol used as the reactant (III) can itself be employed as the diluent. The reaction may require the addition of an acid-binding agent in an equimolar amount. Alkali metal carbonates and alkaline earth metal carbonates, alkaline earth metal hydroxides, metal cyanides, metal fluorides, metal acetates and the like can be used as such acid-binding agents. However, it is possible to dispense with the addition of the acid-binding agent if the alcohols of the formula (III) are employed in the form of their metal alcoholates. These can be employed, for example, as sodium alcoholates or potassium alcoholates in solution in the particular alcohol. However, they can also be produced in an inert solvent from the alcohol and, for example, an elemental alkali metal, an alkali metal hydride or an alkali metal amide, and can be used in the dissolved or undissolved form thus obtained. In place of the alkali metal alcoholates it is also possible to employ other metal alcoholates, for example magnesium alcoholates. The reaction temperatures cab be varied within a wide range. In general, the reaction is carried out at from 0° to the boiling point of the particular solvent, preferably 20° to 100° C. As a rule, the reactants are employed in an equimolar ratio or the reaction is carried out with an excess of the alcohol (III). The acid-binding agent should normally also be present in at least the equimolar amount. Usually, the reactions are carried out under normal pressure but they can also be carried out in closed vessels under the particular autogenous pressure of the solvent used.

In process variant (b), benzo-1,2,4-triazine-3-ether 1-oxides of the formula (IV) are subjected to reduction. The choice of the reducing agent which can be used is restricted since some of the known reducing agents do not bring about a reaction and other known reducing agents lead to excessive reduction to the 1,2-dihydrobenzo-1,2,4-triazine-3ethers. Appropriate reducing agents are readily determined. Amongst the suitable reducing agents, zinc dust in a weakly acid medium, for example dilute acetic acid or an aqueous solution of ammonium chloride, is preferred. Solvents which can be added for this reaction are water-miscible solvents, above all lower alcohols, such as methanol, ethanol or isopropanol. The reaction is generally carried out at 10 to 100° C, preferably at 20° to 80° C.

The reduction in process variant (b) can be carried out by means of catalytically activated hydrogen. In this case the reaction may be carried out using a solution of the compound (IV) in an organic solvent, such as an alcohol, ether, dioxane or tetrahydrofuran. Suitable catalysts include the known hydrogenation catalysts based on nickel, cobalt, palladium, platinum or rhodium. Preferably, inexpensive Raney nickel is used in amounts of 0.01 to 5 mole percent. As a rule, the hydrogenation is carried out in closed vessels under a hydrogen pressure of 0 - 25 atmospheres. The reaction temperature can generally be varied from 0° to 100° C. Preferably the reaction is carried out at 20° to 60° C.

In process variant (c), 1,2-dihydro-benzo-1,2,4-triazine-3-ethers are subjected to mild oxidation. Oxidizing agents which can be used include hydrogen peroxide and the higher valency levels of polyvalent metals, preferably iron-III compounds, for example potassium ferricyanide. The oxidizing agent is employed in at least equimolar amount. The reaction is carried out in aqueous systems and it is possible to add lower alcohols as solubilizing agents. The reactions are carried out at 0° to 100° C, preferably 20° to 80° C.

The following may be mentioned as individual examples of the new active compounds according to the invention: 3-methoxy-7-chloro-benzo-1,2,4-triazine, 3-ethoxy-7-chloro benzo-1,2,4-triazine, 3-propoxy-7-chloro-benzo-1,2,4-triazine, 3-isopropoxy-7-chloro-benzo-1,2,4-triazine, 3-butoxy-7-chlorobenzo-1,2,4-triazine, 3-isobutoxy-7-chloro-benzo-1,2,4-triazine, 3-sec.-butoxy-7-chloro-benzo-1,2,4-triazine, 3-hexyloxy-7-chloro-benzo-1,2,4-triazine, 3-allyloxy-7-chlorobenzo-1,2,4-triazine, 3-(2-chloro-ethoxy)-7-chloro-benzo-1,2,4-triazine, 3-(2,2,2-trichloro-ethoxy)-7-chloro-benzo-1,2,4-triazine, 3-(2-butoxy-ehtoxy)-7-chloro-benzo-1,2,4-triazine, 3-methoxy-7-bromo-benzo-1,2,4-triazine, 3-isopropoxy-7-iodo-benzo-1,2,4-triazine, 3-ethoxy-7-methoxy-benzo-1,2,4-triazine, 3-methoxy-7-ethoxy-benzo-1,2,4-triazine and 3-methoxy-7-trifluoromethyl-benzo-1,2,4-triazine.

The active compounds according to the invention exhibit a powerful fungitoxic action and a bacteriotoxic action. In the concentrations necessary for combating fungi and bacteria they do not damage cultivated plants and they have a low toxicity to warm-blooded animals. For these reasons they are suitable for use as plant protection agents for combating fungi and bacteria. In plant protection, fungitoxic agents are employed in order to combat *Plasmodiophoromycetes, Oomycetes, Chytridiomycetes, Zygomycetes, Ascomycetes, Basidiomycetes* and *Deuteromycetes.*

The active compounds according to the invention can be used against parasitic fungi and bacteria which attack above-ground parts of plants or attack the plants through the soil, and also against seed-borne pathogens. The good action against fungi of the genus *Drechslera* (commonly referred to as *Helminthosporium*), and against the genera *Puccinia, Rhizoctoa, Pythium, Verticillium, Pyricularia* and *Pellicularia* should be mentioned particularly. They also have a significant action against the bacterium *Xanthomonas oryzae,* the pathogen of a disease of rice plants which is widely prevalent in Asia, *Xanthomonas vesicatoria,* species of *Pseudomonas* and species of *Erwinia.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, bactericides, insecticides and acaricides, or nematocides, rodenticides, herbicides, fertilizers, growth-regulating agents, agents for improving the soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

For seed dressing, in general amounts of active compound of 10 mg to 10 g, preferably 100 mg to 3 g, are used per kilogram of seed. For soil treatment, which can be carried out over the entire soil area or in strips or at points, concentrations of active compound of 1 to 1,000 g of active compound per $m^3$ of soil, preferably 10 to 200 g per $m^3$, are generally used at the location where the action is required.

Furthermore, the present invention contemplates methods of selectively killing, combating or controlling pests, e.g. fungi, bacteria, insects and acarids, are more particularly methods of combating fungi and bacteria, which comprises applying to at least one correspondingly (a) such fungi, (b) such bacteria, (c) such insects, (d) such acarids, and (e) the corresponding habitat thereof, i.e. the locus to be protected, e.g. to a growing crop, to an area where a crop is to be grown or to a domestic animal, a correspondingly combative or toxic amount, i.e. a fungicidally, bactericidally, insecticidally or acaricidally effective amount, of the particular active compound of the invention alone or together with a carrier vahicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Mycelium growth test

Nutrient medium used:
20 parts by weight of agar-agar
200 parts by weight of potato decoction
5 parts by weight of malt 15 parts by weight of dextrose
5 parts by weight of peptone
2 parts by weight of disodium hydrogen phosphate
0.3 parts by weight of calcium nitrate
Composition of the solvent mixture:
0.19 part by weight of DMF or acetone
0.01 part by weight of emulsifier (alkylaryl polyglycol ether)

<u>1.80 parts by weight of water</u>
2.00 parts by weight of solvent mixture

Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium which had been cooled to 42° C and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth,
up to 5 medium inhibition of growth
up to 7 slight inhibition of growth
9 growth equal to that of untreated control.

The active compounds, the active compound concentrations and the results can be seen from the following table:

Table 1

| Active Compounds | Active compound concentration in ppm$_{10}$ | Mycelium growth test | | | Fungi and 1 bacterium | | |
|---|---|---|---|---|---|---|---|
| | | Rhizoctonia solani | Pythium ultimum | Verticillium alboatrum | Pyricularia oryzae | Pellicularia sasakii | Xanthomonas oryzae |
| 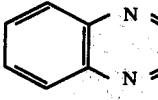 (known) (C) | | 9 | 9 | 9 | 9 | 9 | 9 |
| 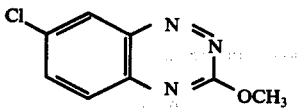 (2) | | 3 | 3 | — | — | 3 | 3 |
| 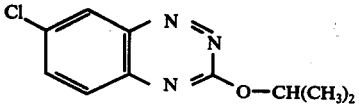 (3) | | 3 | 3 | 3 | 1 | 3 | — |
| 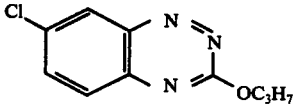 (4) | | — | — | 5 | 3 | 5 | 2 |
| 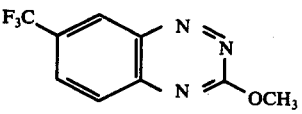 (9) | | — | — | — | — | — | 1 |
| 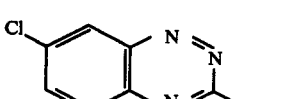 (5) | | — | — | — | — | — | 2 |

Table 1-continued

| Active Compounds | Active compound concentration in ppm[10] | Mycelium growth test ||| Fungi and 1 bacterium |||
|---|---|---|---|---|---|---|---|
| | | Rhizoctonia solani | Pythium ultimum | Verticillium alboatrum | Pyricularia oryzae | Pellicularia sasakii | Xanthomonas oryzae |
| 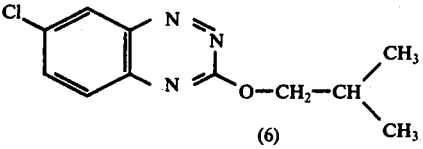 (6) | | — | — | — | — | — | 2 |
| 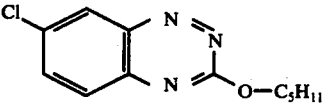 (7) | | — | — | — | — | — | 2 |

EXAMPLE 2

Seed dressing test/stripe disease of barley (see-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by Drechslera graminea (commonly called Helminthosporium gramineum), was shaken with the dressing in a closed glass flask. The seed, on moist filter paper discs in closed Petri dishes, was exposed to a temperature of 4° C for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18° C in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentrations of the active compounds in the dressing, the amounts of dressing used and the number of diseased plants can be seen from the following Table:

Table 2

Seed dressing test/stripe disease of barley

| Active compound | Active compound concentration in the dressing in % by weight | Amount of dressing used in g/kg of seed | Number of plants infected with stripe disease in % of the total plants which have emerged |
|---|---|---|---|
| no dressing | — | — | 45.1 |
| 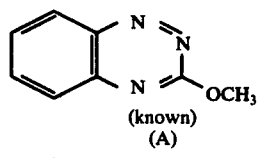 (known) (A) | 25 | 2 | 10.2 |
| 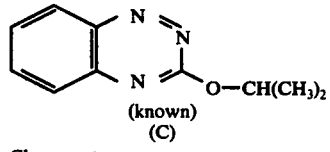 (known) (C) | 25 | 2 | 6.1 |
| 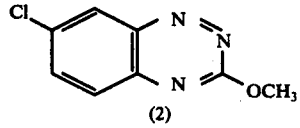 (2) | 25<br>10 | 2<br>2 | 0.0<br>2.0 |
| 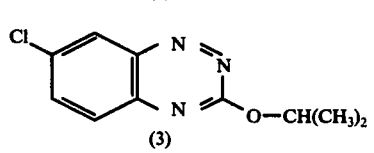 (3) | 25 | 2 | 1.0 |
| 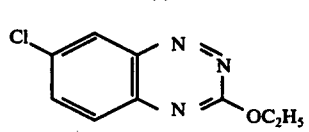 | 25 | 2 | 0.0 |

Table 2-continued

| Active compound | Seed dressing test/stripe disease of barley | | |
|---|---|---|---|
| | Active compound concentration in the dressing in % by weight | Amount of dressing used in g/kg of seed | Number of plants infected with stripe disease in % of the total plants which have emerged |
| (1) 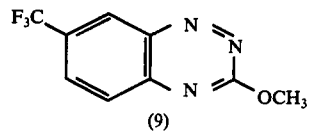 (9) | 25 | 2 | 3.0 |
| 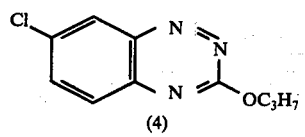 (4) | 25 | 2 | 1.0 |
| 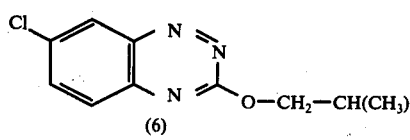 (6) | 25 | 2 | 2.0 |

EXAMPLE 3

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier, and 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dewmoist and were placed, for incubation, in a greenhouse for 24 hours at about 20° C and 100% atomspheric humidity.

After 10 days dwell time of the plants at a temperature of 20° C and 80-90% atmospheric humidity, the occurrence of rust pustules on the plant was evaluated. The degree of infection is expressed as a percentage of the infection of the untreated control plants. 0% denotes no infection and 100% denotes the same degree of infection as in the case of the untreated control. The more active the compound, the lower was the degree of rust infection.

The active compounds, active compound concentrations in the spray liquor and degrees of infection can be seen from the table which follows:

Table 3

| | Shoot treatment test/cereal rust/protective | |
|---|---|---|
| Active compounds | Active compound concentration in the spray liquor in % by weight | Infection in % of the untreated control |
| untreated | — | 100.0 |
| 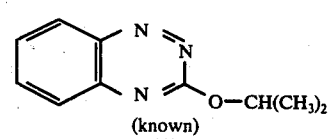 (known) (C) | 0.025 | 75.0 |
| 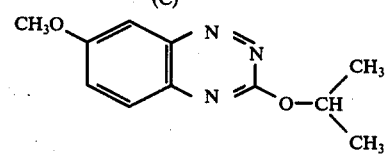 (8) | 0.025 | 12.5 |
| 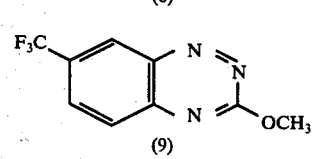 (9) | 0.025 | 0.0 |

Table 3-continued

| Shoot treatment test/cereal rust/protective | | |
|---|---|---|
| Active compounds | Active compound concentration in the spray liquor in % by weight | Infection in % of the untreated control |
| 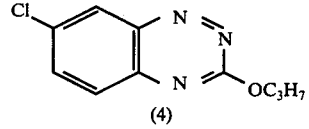 (4) | 0.025 | 25.0 |

EXAMPLE 4

Bacteria test /Xanthomonas oryzae
Solvent: 11.75 parts by weight of acetone
Dispersing agent: 0.75 part by weight of alkylaryl polyglycol ether
Water: 987.50 parts by weight of water
Other additives — parts by weight The amount of active compound required for the desired active compound concentration in the spray liquor was mixed with the stated amount of the solvent and of the dispersing agent and the concentrate was diluted with the stated amount of water.

30 rice plants which were about 30 days old were sprayed with the spray liquor until dripping wet. The plants remained in a greenhouse, at temperatures of 22° to 24° and a relative atmospheric humidity of about 70%, until they had dried. Needles were then dipped into an aqueous bacteria suspension of *Xanthomonoas oryzae* and the plants were inoculated by pricking the leaves. After the inoculation, the leaves stood for 24 hours at 100% relative atmospheric humidity and thereafter in a room at 26° to 28° C and 80% relative atmospheric humidity.

10 days after the inoculation, the infection of all pricked inoculated leaves of plants which had beforehand been treated with the preparation was evaluated, using figures of merit of 1 to 9. 1 denotes 100% action, 3 = good action, 5 = moderate action and 9 = no action.

The active compounds, active compound concentrations and results can be seen from the Table which follows:

Table 4

| Bacteria test/Xanthomonas oryzae | |
|---|---|
| Active compound | Infection at an active compound concentration (in %) of 0.025 |
| untreated control | 9 |
| 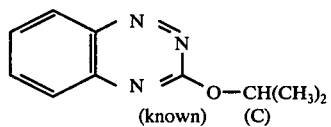 (known) (C) | 9 |
| 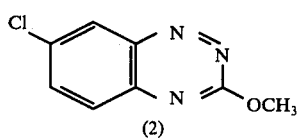 (2) | 3 |
| 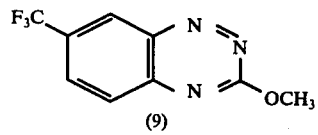 (9) | 3 |
| 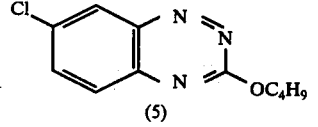 (5) | 1 |
| 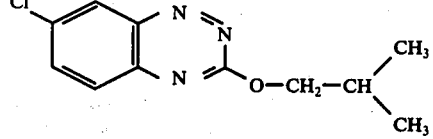 (6) | 2 |
| 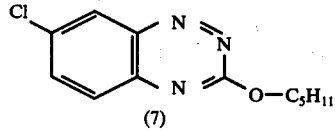 (7) | 4 |
| 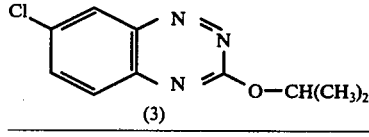 (3) | 5 |

The following further examples are set forth to illustrate, without limitation, the manner of producing the instant compounds according to the present invention:

EXAMPLE 5 a. 3,7-Dichloro-benzo-1,2,4-triazine 1-oxide, which was required as a starting material, and the preparation thereof are described in the literature (see J. Org. Chem. 24, 813–818 (1959); the compound is mentioned and a melting point of 157°–158.5° C is given on page 815; compare also U.S. Pat. No. 2,489,353 which describes the preparation of the 7-chloro-3-hydroxy compound and U.S. Pat. No. 2,489,354 which describes the preparation of the 3,7-dichlorocompound from the above-mentioned substance; and also J. Am. Chem. Soc. 76, 4611–4613 (1954), especially page 4,613 where detailed data on the 3,7-dichloro compound are given; the melting point after recrystallization from ethanol is given as 153°-154° C).

b. A suspension of 21,8 g (0.1 mole) of 3,7-dichlorobenzo-1,2,4-triazine 1-oxide, 7.5 g of zinc dust and 5.5 g of ammonium chloride in 400 ml of water was stirred vigorously at room temperature for 24 hours. 50 ml of glacial acetic acid were then added, the mixture was stirred for a further hour and the insoluble constituents were then filtered off. The latter were extracted twice with methylene chloride. The combined methylene chloride solutions were washed with water, dried over sodium sulfate and evaporated in vacuo. The residue was recrystallized from wash benzine. 7.5 g, that is to say 37% of theory, of 3,7-dichloro-benzo-1,2,4-triazine with a melting point of 113°-115° C were obtained.

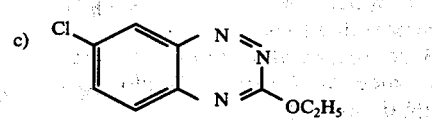

(Preparation according to process variant (a))

A suspension of 20.2 g (0.1 mole) of 3,7-dichlorobenzo-1,2,4-triazine and 12.2 g (0.25 mole) of sodium cyanide in 200 ml of ethanol was boiled under reflux for 2 hours. The salts were filtered off and the filtrate was evaporated in vacuo. The residue was stirred with water and cooled in ice for some time. The crystallized mass was filtered off and recrystallized from wash benzine. 17.6 g, that is to say 84% of theory, of 3-ethoxy-7-chloro-benzo-1,2,4-triazine with a melting point of 90°-92° C were obtained.

EXAMPLE 6 a. Preparation of 3-chloro-benzo-1,2,4triazine-1-oxides required for 3-alkoxy-benzo-1,2,4-triazine 1-oxides:

3-Hydroxy-benzo-1,2,4-triazine 1-oxides which were appropriately substituted in the benzene nucleus were reacted with boiling phosphorus oxychloride. The reaction mixture was worked up according to the instructions given in the literature (J. Org. Chem. 24, 813 (1959)). For example, there were prepared in this way the precursors of the general formula

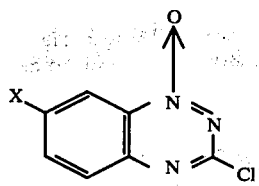

in which X has the following meanings:

Table 5

| | X | Melting point (° C) |
|---|---|---|
| a | Cl | 133-135 |
| b | CH₃O | 162-164 |
| c | CF₃ | 106-108 | b. Preparation of the 3-alkoxy-benzo-1,2,4-triazine 1-oxides required as precursors for process variants (b) and (c):

i. A solution of 0.1 mole of a sodium alcoholate in an adequate excess of the particular alcohol was prepared.

ii. A suspension of 0.1 mole of a sodium alcoholate in toluene was prepared by introducing a suspension of 0.1 mole of sodium anide in portions into a solution of 0.12 mole of an alcohol in 150 ml of toluene. Subsequently nitrogen was passed through the mixture for ½ hour in order to drive off residual ammonia.

0.1 mole of a 3-chloro-benzo-1,2,4-triazine 1-oxide which was substituted in the 7-position was introduced in portions, at room temperature, into a solution or suspension, prepared in this way, of a sodium alcoholate. During this addition, the temperature usually rose to 40° to 45° C. The mixture was then heated to 70° to 80° C for a further 4 hours, the solid constituents were filtered off and the filtrate was evaporated in vacuo. The combined residues were stirred with water and the product was filtered off and recrystallized.

For example, in this way there were obtained the following precursors of the general formula

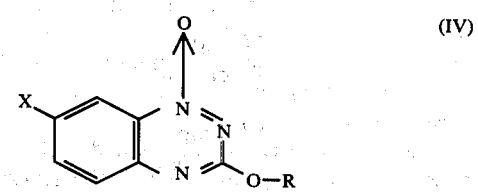

in which R and X were as given in the table below.

Table 6

| | R | X | Melting point (° C) |
|---|---|---|---|
| a | CH₃ | Cl | 158-160 |
| b | C₂H₅ | Cl | 100-102 |
| c | C₃H₇-n | Cl | 103-105 |
| d | C₃H₇-iso | Cl | 120-122 |
| e | C₄H₉-n | Cl | 110-112 |
| f | C₄H₉-iso | Cl | 128-130 |
| g | C₅H₁₁-n | Cl | 101-102 |
| h | C₃H₇-iso | CH₃O | 92- 94 |
| i | CH₃ | CF₃ | 98-100 |
| j | C₃H₇-iso | CF₃ | 150-152 |

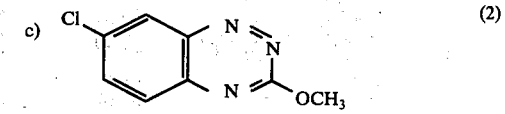

21.2 g (0.1 mole) of 3-methoxy-7-chloro-benzo-1,2,4-triazine 1-oxide and 5 g of Raney nickel in 150 ml of ethanol were initially introduced into a stirred VA autoclave. A pressure of 15 atmospheres of hydrogen was applied at 30° C. The mixture was stirred at 30° to 50° C for 5 hours and during this time further hydrogen was fed in under pressure until the pressure remained constant. The autoclave was let down, the catalyst was filtered off and the filtrate was evaporated in vacuo. The residue was recrystallized from wash benzine. 15.2 g. that is to say 78% of theory, of 3-methoxy-7-chlorobenzo-1,2,4-triazine with a melting point of 122° C were obtained.

EXAMPLE 7 a. A mixture of 21.15 g (0.1 mole) of 3-methoxy-7-chloro-benzo-1,2,4-triazine 1-oxide, 200 ml of methanol, 30 ml of concentrated hydrochloric acid, 150 ml of water and 25 g of granulated tin was heated under reflux for 2 hours. During this time the reaction mixture gradually became colorless. The solution was decanted from unreacted tin and cooled in ice for a prolonged period. The crystals which had separated out and which consisted of the hydrochloride of 3-methoxy-7-chloro-1,2-dihydro-benzo-1,2-triazine were filtered off.

b) 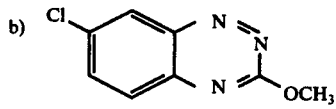 (2)

(Preparation according to process variant (c))

3-Methoxy-7-chloro-1,2-dihydro-benzo-1,2,4-triazine hydrochloride, obtained as described above, was dissolved in 250 ml of warm water. A solution of 100 g of potassium ferricyanide and 30 g of sodium hydroxide in 500 ml of water was allowed to run into this solution at 35°–40° C. The mixture was stirred for a further hour at 35° to 40° C, then cooled with ice and filtered. 9.2 g, that is to say 47% of theory, of 3-methoxy-7-chloro-benzo-1,2,4-triazine with a melting point of 121°–122° C were obtained on recrystallization of the crystals from wash benzine.

Analogously to Examples 5, 6 and 7, there were obtained the following compounds of the general formula

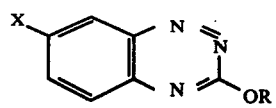

in which R and X were as given in the table below.

| Compound No. | R | X | Melting point (° C) | Preferred preparation process |
|---|---|---|---|---|
| 3 | iso-$C_3H_7$ | Cl | 72–74 | b) |
| 4 | n-$C_3H_7$ | Cl | 82–84 | b) |
| 5 | n-$C_4H_9$ | Cl | 47–49 | b) |
| 6 | iso-$C_4H_9$ | Cl | 70–72 | b) |
| 7 | $C_5H_{11}$ | Cl | 66–68 | b) |
| 8 | iso-$C_3H_7$ | $CH_3O$ | 75–77 | b) |
| 9 | $CH_3$ | $CF_3$ | 76–78 | b) |
| 10 | iso-$C_3H_7$ | $CF_3$ | 100–102 | b) |

Other compounds which can be similarly prepared include:

Table 8

| R | X |
|---|---|
| sec.-$C_4H_9$ | Cl |
| $C_6H_{13}$ | Cl |
| $CH_2$—CH=$CH_2$ | Cl |
| $CH_2$—$CCl_3$ | Cl |
| $C_2H_4$—O—$C_4H_9$ | Cl |
| $CH_3$ | Br |
| $C_3H_7$-iso | I |
| $C_2H_5$ | $CH_3O$ |
| $CH_3$ | $C_2H_5O$ |

It will be appreciated that the instant specification and examples are set forth by way of illustration and not limitation, and that various modifications and changes may be made without departing from the spirit and scope of the present invention.

What is claimed is:

1. A benzo-1,2,4-triazine-3-ether of the formula

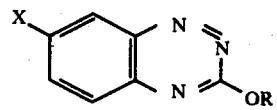

in which
R is alkyl with up to 8 carbon atoms optionally substituted by halogen or lower alkoxy, or alkenyl with 3 to 6 carbon atoms, and
X is halogen, trifluoromethyl or alkoxy with up to 4 carbon atoms.

2. A compound according to claim 1 in which R is alkyl with up to 6 carbon atoms optionally substituted by chlorine, bromine or alkoxy with up to 4 carbon atoms, or alkenyl with 3 to 6 carbon atoms, and X is chlorine, bromine, trifluoromethyl or alkoxy with up to 3 carbon atoms.

3. A compound according to claim 1, wherein such compound is 3-methoxy-7-chloro-benzo-1,2,4-triazine of the formula

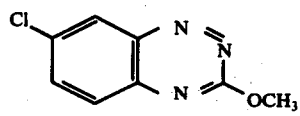

4. A compound according to claim 1, wherein such compound is 3-isopropoxy-7-chloro-benzo-1,2,4-triazine of the formula

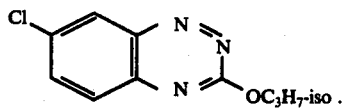

5. A compound according to claim 1, wherein such compound is 3-propoxy-7-chloro-benzo-1,2,4-triazine of the formula

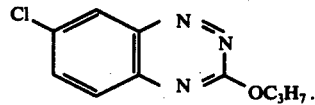

6. A compound according to claim 1, wherein such compound is 3-isobutoxy-7-chloro-benzo-1,2,4-triazine of the formula

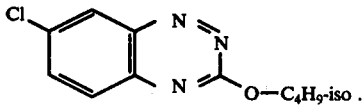

7. A compound according to claim 1, wherein such compound is 3-methoxy -7-trifluoromethyl-benzo-triazine-1,2,4 of the formula

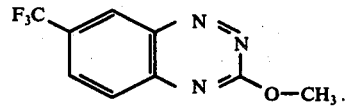

8. A fungicidal, bactericidal, insecticial or acaricidal composition containing as active ingredient a fungicidally, bactericidally, insecticidally or acaricidally effective amount of a compound according to claim 1 in admixture with a diluent.

9. A method of combating fungus, bacterium, insect or acarid pests which comprises applying to the pests or a habitat thereof a fungicidally, batericidally, insecticidally or acaricidally effective amount of a compound according to claim 1.

10. The method according to claim 9 in which said compound is
3-methoxy-7-chloro-benzo-1,2,4-triazine,
3-isopropoxy-7-chloro-benzo-1,2,4-triazine,
3-propoxy-7-chloro-benzo-1,2,4-triazine,
3-isobutoxy-7-chloro-benzo-1,2,4-triazine, or
3-methoxy -7-trifluoromethyl-benzo-triazine-1,2,4.

* * * * *